United States Patent
Takaishi et al.

(10) Patent No.: US 8,293,681 B2
(45) Date of Patent: Oct. 23, 2012

(54) SEED TREATMENT AGENT AND METHOD FOR PROTECTING PLANT

(75) Inventors: Masanao Takaishi, Toyonaka (JP); Makoto Kurahashi, Nishinomiya (JP)

(73) Assignee: Sumitomo Chemical Company, Ltd., Tokyo (JP)

( * ) Notice: Subject to any disclaimer, the term of this patent is extended or adjusted under 35 U.S.C. 154(b) by 0 days.

(21) Appl. No.: 13/119,622

(22) PCT Filed: Sep. 17, 2009

(86) PCT No.: PCT/JP2009/066837
§ 371 (c)(1), (2), (4) Date: Apr. 29, 2011

(87) PCT Pub. No.: WO2010/032873
PCT Pub. Date: Mar. 25, 2010

(65) Prior Publication Data
US 2011/0197318 A1    Aug. 11, 2011

(30) Foreign Application Priority Data

Sep. 19, 2008 (JP) .................................. 2008-241610

(51) Int. Cl.
*A01N 25/26* (2006.01)
*A01N 37/18* (2006.01)
(52) U.S. Cl. ........................................ 504/100; 504/336
(58) Field of Classification Search ........................ None
See application file for complete search history.

(56) References Cited

U.S. PATENT DOCUMENTS

| | | | |
|---|---|---|---|
| 5,948,819 A | 9/1999 | Ohtsuka et al. | |
| 6,689,356 B1 | 2/2004 | Zlotkin et al. | |

FOREIGN PATENT DOCUMENTS

| | | | |
|---|---|---|---|
| CA | 2199422 A1 | 3/1996 | |
| EP | 0353191 A2 | 1/1990 | |
| EP | 0374753 A2 | 6/1990 | |
| EP | 0392225 A2 | 10/1990 | |
| EP | 0427529 A1 | 5/1991 | |
| EP | 0451878 A1 | 10/1991 | |
| EP | 0754672 | * 1/1997 | |
| EP | 0754672 A1 | 1/1997 | |
| EP | 2253206 A1 | 11/2010 | |
| WO | 93/07278 A1 | 4/1993 | |
| WO | 95/27693 A1 | 10/1995 | |
| WO | 95/33818 A2 | 12/1995 | |
| WO | 95/34656 A1 | 12/1995 | |
| WO | 96/07633 A1 | 3/1996 | |
| WO | 03/000906 A2 | 1/2003 | |
| WO | 03/052073 A2 | 6/2003 | |
| WO | 2009/116658 A1 | 9/2009 | |
| WO | 2009/119872 A2 | 10/2009 | |
| WO | WO 2009119872 | * 10/2009 | |

OTHER PUBLICATIONS

Communication: International Search Report for International Patent Application No. PCT/JP2009/066837 mailed Jan. 26, 2010.

* cited by examiner

*Primary Examiner* — Alton Pryor

(57) ABSTRACT

PROBLEM Provided is a seed treatment agent having excellent control effect on plant diseases and a method for protecting a plant from plant diseases. SOLUTION A seed treatment agent comprising, as an active ingredient, an α-methoxyphenylacetic acid compound represented by formula (1).

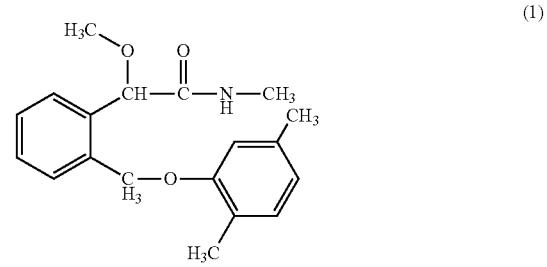

(1)

3 Claims, No Drawings

SEED TREATMENT AGENT AND METHOD FOR PROTECTING PLANT

This application is a national stage of PCT/JP2009/066837, filed on Sep. 17, 2009, which claims priority to Japanese Patent Application No. 2008-241610, filed on Sep. 19, 2008. Each of these documents is incorporated herein by reference in its entirety.

TECHNICAL FIELD

The present invention relates to a seed treatment agent and method for protecting a plant.

BACKGROUND ART

α-Substituted phenylacetic acid compounds are conventionally known as an active ingredient of a fungicide (for example, see PATENT DOCUMENT 1).
PATENT DOCUMENT 1: International Publication WO 95/27,693

DISCLOSURE OF THE INVENTION

Problems to be Solved by the Invention

An object of the present invention is to provide a seed treatment agent having excellent control effect for plant diseases and a method for protecting a plant from plant diseases.

Means for Solving the Problems

The present invention provides a method for protecting a plant from plant diseases by treating a seed of a plant with an α-methoxyphenylacetic acid compound represented by the following formula (1) and a seed treatment agent for use in the method.

That is, the present invention adopts the following constitutions:

[1] A seed treatment agent comprising, as an active ingredient, an α-methoxyphenylacetic acid compound represented by formula (1):

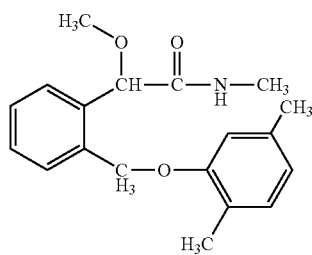

(1)

[2] A method for protecting a plant from plant diseases which comprises treating a seed of a plant with an effective amount of an α-methoxyphenylacetic acid compound represented by formula (1) of [1].

[3] The method for protecting a plant according to [2] wherein the plant is a seed or a bulb of gramineous plants, legume plants, brassicaceous plants, chenopodiaceous plants, malvaceous plant or solanaceae plants.

[4] A plant seed or a bulb treated with an effective amount of an α-methoxyphenylacetic acid compound represented by formula (1) of [1].

[5] Use of an α-methoxyphenylacetic acid compound represented by formula (1) of [1] in a plant seed treatment for protecting a plant from plant diseases.

A plant can be protected from plant diseases by treating a seed or a bulb of the plant with a seed treatment agent according to the present invention.

BEST MODE FOR CARRYING OUT THE INVENTION

The α-methoxyphenylacetic acid compound represented by formula (1) for use in the present invention is described. The aspects of the α-methoxyphenylacetic acid compound represented by formula (1) are as follows.

The α-methoxyphenylacetic acid compound represented by formula (1) has isomers such as stereoisomers such as optical isomers based on an asymmetric carbon atoms and tautomers. Any isomer can be contained and used solely or in a mixture of any isomer ratio in the present invention.

An optical active material or a racemic body of the α-methoxyphenylacetic acid compound represented by formula (1) can be used in the present invention.

The α-methoxyphenylacetic acid compound represented by formula (1) may be in a form of a solvate (for example, hydrate). It can be used in a form of a solvate in the present invention.

The α-methoxyphenylacetic acid compound represented by formula (1) may be in a form of a crystal form and/or an amorphous form. It can be used in any form in the present invention.

The α-methoxyphenylacetic acid compound represented by formula (1) is a compound described in WO95/27,693 pamphlet. These compounds can be synthesized, for example, by a method described in the pamphlet.

The seed treatment agent according to the present invention can be used, for example, to the seed or the bulb of the following plants. Here, the bulb means a bulb, corm, rhizoma, stem tuber, root tuber and rhizophore.

Examples of the plant are as follows:

crops: corn, rice, wheat, barley, rye, oat, sorghum, cotton, soybean, peanut, buckwheat, beet, rapeseed, sunflower, sugar cane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, *Dioscorea japonica*, colocasia, etc., flowers, foliage plants, turf grasses, fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, coconuts, etc., trees other than fruit trees; tea, mulberry, flowering plant, roadside trees (ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus cuspidate*), etc.

The aforementioned plants include plants, to which resistance to HPPD inhibitors such as isoxaflutole, ALS inhibitors such as imazethapyr or thifensulfuron-methyl, EPSP synthetase inhibitors, glutamine synthetase inhibitors, and herbicides such as bromoxynil, dicamba, etc. has been conferred by a classical breeding method or genetic engineering technique.

Examples of a plant on which resistance has been conferred by a classical breeding method include Clearfield (registered trademark) Canola resistant to imidazolinone herbicides such as imazethapyr, and STS soy bean resistant to sulfonylurea ALS inhibitory herbicides such as thifensulfuron-methyl. In addition, examples of a plant on which resistance has been conferred by genetic engineering technology include corn, soy bean, cotton, rape resistant to glyphosate and glufosinate, which is already commercially available under a product name of RoundupReady (registered trademark), Rounup Ready 2 (registered trademark), and LibertyLink (registered trademark).

The aforementioned plants include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3 or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Moreover, toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1 or Cry9C, and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to *Coleoptera, Diptera* and *Lepidoptera*, to the plants.

Furthermore, genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Bt11 corn borer (CB) trait), and Protecta (registered trademark).

The aforementioned plants also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906).

The plant mentioned above may include a line on which two or more characters relating to resistance to herbicides, resistance to harmful insects, resistance to diseases and so on as described above have been conferred using classic breeding technology or genetic engineering technology; and a line on which two or more characters of the parental lines have been conferred by crossing genetically engineered plants having similar or different characters.

The seed treatment agent according to the present invention is effective for the following plant diseases, for example.

Diseases of rice: blast (*Magnaporthe grisea*), *Helminthosporium* leaf spot (*Cochliobolus miyabeanus*), sheath blight (*Rhizoctonia solani*), and bakanae disease (*Gibberella fujikuroi*).

Diseases of wheat: powdery mildew (*Erysiphe graminis*), *Fusarium* head blight (*Fusarium graminearum, F. avenacerum, F. culmorum, Microdochium nivale*), rust (*Puccinia striiformis, P. graminis, P. recondita*), pink snow mold (*Micronectriella nivale*), *Typhula* snow blight (*Typhula* sp.), loose smut (*Ustilago tritici*), bunt (*Tilletia caries*), eyespot (*Pseudocercosporella herpotrichoides*), leaf blotch (*Mycosphaerella graminicola*), glume blotch (*Stagonospora nodorum*), and yellow spot (*Pyrenophora tritici-repentis*).

Diseases of barley: powdery mildew (*Erysiphe graminis*), *Fusarium* head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and *Rhizoctonia* damping-off (*Rhizoctonia solani*).

Diseases of corn: smut (*Ustilago maydis*), brown spot (*Cochliobolus heterostrophus*), copper spot (*Gloeocercospora sorghi*), southern rust (*Puccinia polysora*), gray leaf spot (*Cercospora zeae-maydis*), and *Rhizoctonia* damping-off (*Rhizoctonia solani*).

Diseases of citrus: melanose (*Diaporthe citri*), scab (*Elsinoe fawcetti*), *penicillium* rot (*Penicillium digitatum, P. italicum*), and brown rot (*Phytophthora parasitica, Phytophthora citrophthora*).

Diseases of apple: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), crown rot (*Phytophtora cactorum*).

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*);

Diseases of peach: brown rot (*Monilinia fructicola*), scab (*Cladosporium carpophilum*), and *phomopsis* rot (*Phomopsis* sp.).

Diseases of grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Diseases of Japanese persimmon: anthracnose (*Gloeosporium kaki*), and leaf spot (*Cercospora kaki, Mycosphaerella nawae*).

Diseases of gourd: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora* sp.), and damping-off (*Pythium* sp.);

Diseases of tomato: early blight (*Alternaria solani*), leaf mold (*Cladosporium fulvum*), and late blight (*Phytophthora infestans*).

Diseases of eggplant: brown spot (*Phomopsis vexans*), and powdery mildew (*Erysiphe cichoracearum*).

Diseases of cruciferous vegetables: *Alternaria* leaf spot (*Alternaria japonica*), white spot (*Cercosporella brassicae*), clubroot (*Plasmodiophora brassicae*), and downy mildew (*Peronospora parasitica*).

Diseases of welsh onion: rust (*Puccinia allii*), and downy mildew (*Peronospora destructor*).

Diseases of soybean: purple seed stain (*Cercospora kikuchii*), sphaceloma scad (*Elsinoe glycines*), pod and stem blight (*Diaporthe phaseolorum* var. *sojae*), septoria brown spot (*Septoria glycines*), frogeye leaf spot (*Cercospora sojina*), rust (*Phakopsora pachyrhizi*), brown stem rot (*Phytophthora sojae*), and *Rhizoctonia* damping-off (*Rhizoctonia solani*).

Diseases of kidney bean: anthracnose (*Colletotrichum lindemthianum*).

Diseases of peanut: leaf spot (*Cercospora personata*), brown leaf spot (*Cercospora arachidicola*) and southern blight (*Sclerotium rolfsii*).

Diseases of garden pea: powdery mildew (*Erysiphe pisi*), and root rot (*Fusarium solani* f. sp. *pisi*).

Diseases of potato: early blight (*Alternaria solani*), late blight (*Phytophthora infestans*), pink rot (*Phytophthora erythroseptica*) and powdery scab (*Spongospora subterranean* f. sp. *subterranea*).

Diseases of strawberry: powdery mildew (*Sphaerotheca humuli*), and anthracnose (*Glomerella cingulata*).

Diseases of tea: net blister blight (*Exobasidium reticulatum*), white scab (*Elsinoe leucospila*), gray blight (*Pestalotiopsis* sp.), and anthracnose (*Colletotrichum theae-sinensis*).

Diseases of tobacco: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Diseases of rapeseed: *sclerotinia* rot (*Sclerotinia sclerotiorum*), and *Rhizoctonia* damping-off (*Rhizoctonia solani*).

Diseases of cotton: *Rhizoctonia* damping-off (*Rhizoctonia solani*).

Diseases of sugar beet: *Cercospora* leaf spot (*Cercospora beticola*), leaf blight (*Thanatephorus cucumeris*), Root rot (*Thanatephorus cucumeris*), and *Aphanomyces* root rot (*Aphanomyces cochlioides*).

Diseases of rose: black spot (*Diplocarpon rosae*), powdery mildew (*Sphaerotheca pannosa*), and downy mildew (*Peronospora sparsa*).

Diseases of chrysanthemum and asteraceous plants: downy mildew (*Bremia lactucae*), leaf blight (*Septoria chrysanthemi-indici*), and white rust (*Puccinia horiana*).

Diseases of various groups: diseases caused by *Pythium* spp. (*Pythium aphanidermatum, Pythium debarianum, Pythium graminicola, Pythium irregulare, Pythium ultimum*), gray mold (*Botrytis cinerea*), and *Sclerotinia* rot (*Sclerotinia sclerotiorum*).

Disease of Japanise radish: *Alternaria* leaf spot (*Alternaria brassicicola*).

Diseases of turfgrass: dollar spot (*Sclerotinia homeocarpa*), and brown patch and large patch (*Rhizoctonia solani*).

Disease of banana: sigatoka (*Mycosphaerella fijiensis, Mycosphaerella musicola*).

Disease of sunflower: downy mildew (*Plasmopara halstedii*).

Seed diseases or diseases in the early stages of the growth of various plants caused by bacteria of *Aspergillus* genus, *Penicillium* genus, *Fusarium* genus, *Gibberella* genus, *Tricoderma* genus, *Thielaviopsis* genus, *Rhizopus* genus, *Mucor* genus, *Corticium* genus, *Phoma* genus, *Rhizoctonia* genus and *Diplodia* genus.

Viral diseases of various plants mediated by *Polymixa* genus or the *Olpidium* genus and so on.

The seed treatment agent according to the present invention is expected to have high control effect particularly on plant diseases which occur in corn, sorghum, rice, rape, soy bean, potato, sugar beet and cotton among the above. Among plant diseases occurring in these plants, plant diseases on which particularly high effects are expected include diseases by *Rhizoctonia*, diseases by *Pythium* and diseases by *Fusarium*.

The seed treatment agent according to the present invention may consist of the α-methoxyphenylacetic acid compound represented by formula (1) alone, but typically the α-methoxyphenylacetic acid compound represented by formula (1) is mixed with an inert carrier suitable for seed treatment along with a surfactant and other formulation auxiliary agents as needed so that the mixture is formulated into an oil agent, an emulsion, a flowable agent, a wettable powder, a granulated wettable powder, a powder agent and so on. The α-methoxyphenylacetic acid compound represented by formula (1) is contained in such a seed treatment agent typically in the range of 0.1 to 99% by weight, preferably 0.2 to 90% by weight.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

Treatment of a seed or a bulb in the present invention is, for example, a method for treating a seed or a bulb of a plant to be protected from plant diseases with a seed treatment agent of the present invention and specific examples thereof include a spraying treatment in which a suspension of the seed treatment agent of the present invention is atomized and sprayed on the seed surface or the bulb surface; smearing treatment in which a wettable powder, an emulsion, a flowable agent or the like of the seed treatment agent of the present invention as it is or added with a small amount of water is applied on the seed surface or the bulb surface; immersing treatment in which the seed is immersed in a solution of the seed treatment agent of the present invention for a certain period of time; film coating treatment and pellet coating treatment.

In the case of the spraying treatment and the smearing treatment, the emulsion, wettable powder or suspension is applied after diluted with water or as it is without dilution and the powder agent is typically applied as it is without dilution. The concentration of the α-methoxyphenylacetic acid compound represented by formula (1) is typically from 0.01 to 99%, preferably from 0.05 to 90%. The volume ratio of the seed to the treatment liquid is from 1:0.0005 to 1:0.05, preferably from 1:0.001 to 1:0.02 assuming the volume of the seed to be 1. The application amount of the α-methoxyphenylacetic acid compound represented by formula (1) is typically from 0.001 to 20 g, preferably from 0.01 to 5 g for 1 kg of the seed.

In the case of the immersing treatment, the formulation is typically diluted with water and used, and the concentration of the α-methoxyphenylacetic acid compound represented by formula (1) is typically from 0.0001 to 99%, preferably from 0.001 to 90%. The volume ratio of the seed to the treatment liquid is from 1:1 to 1:100, preferably from 1:2 to 1:20 assuming the volume of the seed to be 1. The immersion time typically 1 minute to 48 hours and the immersion temperature is typically from 0 to 40° C., preferably from 5 to 25° C.

EXAMPLES

In the following, the present invention will be more specifically described by way of formulation examples, treatment formulation examples, and test examples. However, the present invention is not limited to the following examples. In the following examples, the part represents part by weight unless otherwise noted in particular.

(R)-α-methoxyphenylacetic acid compound (1a) having the R type steric structure according to the Cahn-Ingold-Prelog rule represented by the following formula (1a) and the racemic body (1b) of the α-methoxyphenylacetic acid compound are used as the α-methoxyphenylacetic acid compound represented by the formula (1).

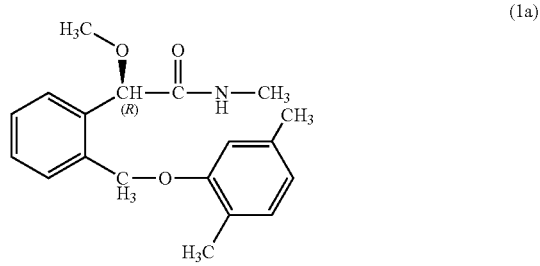

Formulation Example 1

2.5 Parts of the compound (1a) or the compound (1b), 14 parts of polyoxyethylene styrylphenyl ether, 6 parts of calcium dodecyl benzene sulfonate and 83.5 parts of xylene are fully mixed, so as to obtain respective emulsions.

Formulation Example 2

5 Parts of the compound (1a) or the compound (1b), 35 parts of a mixture of white carbon and a polyoxyethylene alkyl ether sulfate ammonium salt (weight ratio 1:1) and 60 parts of water are mixed, and the mixture is subjected to fine grinding according to a wet grinding method, so as to obtain respective flowables.

Formulation Example 3

5 Parts of the compound (1a) or the compound (1b), 1.5 parts of sorbitan trioleate and 38.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowables.

Formulation Example 4

40 Parts of the compound (1a) or the compound (1b), 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant slurry is filtered to remove the glass beads and respective flowables are obtained.

Formulation Example 5

50 Parts of the compound (1a) or the compound (1b), 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix is ground with a jet mill so as to obtain respective powders.

Formulation Example 6

12.5 Parts of the compound (1a) or the compound (1b), 3 parts of calcium lignin sulfonate, 2 parts of sodium lauryl sulfate and 84.5 parts of synthetic hydrated silicon oxide are fully ground and mixed so as to obtain respective wettable powders.

Formulation Example 7

1 Part of the compound (1a) or the compound (1b), 87 parts of kaolin clay and 12 parts of talc are fully ground and mixed so as to obtain respective powders.

Treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Treatment Example 2

An emulsion prepared as in Formulation example 1 is used for smear treatment in an amount of 500 ml per 100 kg of dried sugar beet seeds using a rotary seed treatment machine (seed dresser, produced by Hans-Ulrich Hege GmbH) so as to obtain treated seeds.

Treatment Example 3

A flowable prepared as in Formulation example 2 is used for smear treatment in an amount of 50 ml per 10 kg of dried rape seeds using a rotary seed treatment machine (seed dresser, produced by Hans-Ulrich Hege GmbH) so as to obtain treated seeds.

Treatment Example 4

A flowable prepared as in Formulation example 2 is used for smear treatment in an amount of 500 ml per 100 kg of dried soy bean seeds using a rotary seed treatment machine (seed dresser, produced by Hans-Ulrich Hege GmbH) so as to obtain treated seeds.

Treatment Example 5

A flowable prepared as in Formulation example 3 is used for smear treatment in an amount of 40 ml per 10 kg of dried corn seeds using a rotary seed treatment machine (seed dresser, produced by Hans-Ulrich Hege GmbH) so as to obtain treated seeds.

Treatment Example 6

A flowable prepared as in Formulation example 3 is used for smear treatment in an amount of 500 ml per 100 kg of dried corn seeds using a rotary seed treatment machine (seed dresser, produced by Hans-Ulrich Hege GmbH) so as to obtain treated seeds.

Treatment Example 7

10 Parts of a flowable prepared as in Formulation example 4, 10 parts of pigment BPD6135 (manufactured by Sun Chemical) and 80 parts of water are mixed and the resultant mixture is used for smear treatment in an amount of 60 ml per 10 kg of dried rice seeds using a rotary seed treatment machine (seed dresser, produced by Hans-Ulrich Hege GmbH) so as to obtain treated seeds.

Treatment Example 8

5 Parts of a flowable prepared as in Formulation example 4, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Treatment Example 9

A powder prepared as in Formulation example 5 is used for powder coating treatment in an amount of 50 g per 10 kg of dried cotton seeds so as to obtain treated seeds.

Treatment Example 10

1 part of a flowable prepared as in Formulation example 2 and 99 parts of water are mixed and 1 kg of rice seeds are immersed in 3,000 ml of the diluted liquid for 24 hours to obtain treated seeds.

Test Example 1

10 μl of a dimethylsulphoxide solution of the compound (1b) and 10 g of pea (*Waiseiakabanakinusaya*) seeds were put in a 50 ml tube and mixed to allow the compound (1b) to stick to the surface of the seeds and then the mixture was allowed to stand still overnight to obtain treated seeds of the present invention. A plastic pot was filled with sandy soil, and the treated seeds of the present invention were disseminated. Then the seeds were covered with sandy soil, which had been mixed with a bran medium on which root rot on pea (*Fusarium solani* f. sp. *pisi*) had been allowed to grow and the peas were grown in a greenhouse of from 22 to 24° C. for six days while sprinkling water appropriately. A spore suspension of root rot on pea was perfused on the root of the seedlings for inoculation and the peas were allowed to grow in a greenhouse for further six days and the control effect was checked.

Besides, the incidence of disease was also checked in the case of seeds without the treatment with the agent in order to calculate the control value.

The incidence of disease was calculated by Equation 1 and the control value was calculated by Equation 2 based on the incidence of disease.

The results are shown in Table 1.

Incidence of disease=(Number of no budding seeds and number of seedlings in which development of disease was observed)×100/(Number of total disseminated seeds)      "Equation 1"

Control value=$100\times(A-B)/A$      "Equation 2"

A: Incidence of disease of plant in untreated area
B: Incidence of disease of plant in treated area

TABLE 1

| Test compound | Active ingredient concentration (gai/100 kg seed) | Incidence of disease | Control value |
|---|---|---|---|
| Compound (1b) | 10 | 0 | 100 |
| Not treated with agent | — | 33 | — |

Test Example 2

The flowable of the compound (1a) and the flowable of the compound (1b) were diluted with water to prepare an agent solution containing the compound (1a) or compound (1b). Unhulled rice seeds (*Tanginbozu*) affected with rice 'Bakanae' disease was immersed in the agent solution for 24 hours and then the unhulled rice seeds were taken out of the agent solution and air dried to obtain treated seeds. The treated seeds were immersed in water at 12° C. for 4 days and subsequently in water at 30° C. overnight. A plastic pot was filled with sandy soil, and the treated seeds were disseminated and allowed to grow in a greenhouse at 26° C. for 23 days to investigate the control effect.

Besides, the incidence of disease was also checked in the case of seeds without the treatment with the agent in order to calculate the control value.

The incidence of disease was calculated by Equation 3 and the control value was calculated based on the incidence of disease by Equation 2.

The results are shown in Table 2.

Incidence of disease=(Number of seedlings in which development of disease was observed)×100/ (Number of total seedlings)  "Equation 3"

TABLE 2

| Test compound | Active ingredient concentration (ppm) | Incidence of disease | Control value |
| --- | --- | --- | --- |
| Compound (1b) | 2000 | 1.3 | 93 |
| Compound (1b) | 500 | 1.6 | 92 |
| Compound (1b) | 125 | 1.4 | 93 |
| Compound (1b) | 62.5 | 0.9 | 95 |
| Not treated with agent | — | 19.2 | — |

Test Example 3

10 μl of a dimethylsulphoxide solution of the compound (1a) or compound (1b) and 10 g of pea (*Waiseiakabanakinusaya*) seeds were put in a 50 ml tube and mixed to allow the compound (1a) or compound (1b) to stick to the surface of the seeds and then the mixture was allowed to stand still overnight to obtain treated seeds of the present invention. A plastic pot was filled with sandy soil, and the treated seeds of the present invention were disseminated. Then the seeds were covered with sandy soil, which had been mixed with a bran medium on which root rot on pea (*Fusarium solani* f. sp. *pisi*) had been allowed to grow and the peas were grown in a greenhouse of from 22 to 24° C. for six days while sprinkling water appropriately. A spore suspension of root rot on pea was perfused on the root of the seedlings for inoculation and the peas were allowed to grow in a greenhouse for further six days and the control effect was checked.

Besides, the incidence of disease was also checked in the case of seeds without the treatment with the agent in order to calculate the control value. Also, 2-[2-(2-methyl-phenoxymethyl)-phenyl]-2-methoxy-N-methyl-acetamide, which is described in International Publication WO 95/27,693 and hereinafter referred to as compound A, and 2-[2-(2-chloro-5-methyl-phenoxymethyl)-phenyl]-2-methoxy-N-methyl-acetamide, which is described in International Publication WO 96/07,633 and hereinafter referred to as compound B, were used as reference compounds.

The incidence of disease was calculated by Equation 1 and the control value was calculated by Equation 2 based on the incidence of disease.

The results are shown in Table 3.

TABLE 3

| Test compound | Active ingredient concentration (gai/100 kg seed) | Incidence of disease | Control value |
| --- | --- | --- | --- |
| Compound (1a) | 10 | 0 | 100 |
| Compound (1a) | 2.5 | 4 | 97 |
| Compound (1b) | 10 | 0 | 100 |
| Compound (1b) | 2.5 | 10 | 81 |
| Compound A | 10 | 7 | 87 |
| Compound A | 2.5 | 23 | 57 |
| Compound B | 10 | 10 | 81 |
| Compound B | 2.5 | 20 | 62 |
| Not treated with agent | — | 53 | 0 |

INDUSTRIAL APPLICABILITY

A plant can be protected from plant diseases by treating a seed of the plant with an effective amount of an α-methoxyphenylacetic acid compound represented by formula (1).

The invention claimed is:

1. A method for protecting a plant from plant diseases which comprises treating a seed of a plant with an effective amount of an α-methoxyphenylacetic acid compound represented by formula (1):

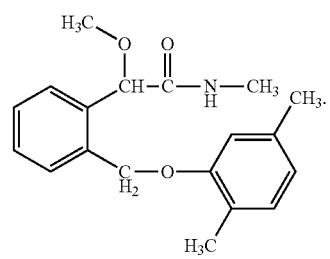

(1)

2. The method for protecting a plant according to claim 1 wherein the plant is a seed of gramineous plants, legume plants, brassicaceous plants, chenopodiaceous plants, malvaceous plant or solanaceae plants.

3. A plant seed treated with an effective amount of an α-methoxyphenylacetic acid compound represented by formula (1):

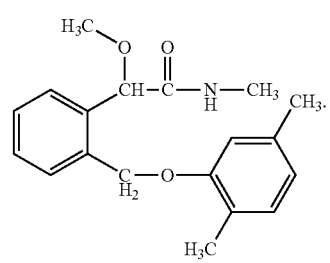

(1)

* * * * *